United States Patent
Pan et al.

(10) Patent No.: US 10,444,237 B2
(45) Date of Patent: Oct. 15, 2019

(54) ANTI-PANCREATIC CANCER MONOCLONAL ANTIBODY AND USE THEREOF

(71) Applicant: NANJING MARKERLINE BIOMEDICAL TECHNOLOGY CO., LTD., Nanjing, Jiangsu (CN)

(72) Inventors: Yue Pan, Nanjing (CN); Shiyang Pan, Nanjing (CN); Jian Xu, Nanjing (CN)

(73) Assignee: NANJING MARKERLINE BIOMEDICAL TECHNOLOGY CO., LTD., Nanjing, Jiangsu (CN)

( * ) Notice: Subject to any disclaimer, the term of this patent is extended or adjusted under 35 U.S.C. 154(b) by 0 days.

(21) Appl. No.: 15/749,490

(22) PCT Filed: Jul. 26, 2016

(86) PCT No.: PCT/CN2016/091737
§ 371 (c)(1),
(2) Date: Jan. 31, 2018

(87) PCT Pub. No.: WO2017/020752
PCT Pub. Date: Feb. 9, 2017

(65) Prior Publication Data
US 2018/0224457 A1    Aug. 9, 2018

(30) Foreign Application Priority Data

Jul. 31, 2015    (CN) .......................... 2015 1 0466976

(51) Int. Cl.
G01N 33/574    (2006.01)
C07K 16/30    (2006.01)
C12N 5/12    (2006.01)
G01N 33/577    (2006.01)
A61P 35/00    (2006.01)

(52) U.S. Cl.
CPC ........ G01N 33/57438 (2013.01); A61P 35/00 (2018.01); C07K 16/303 (2013.01); C12N 5/12 (2013.01); G01N 33/577 (2013.01); *G01N 2800/067* (2013.01); *G01N 2800/50* (2013.01); *G01N 2800/52* (2013.01)

(58) Field of Classification Search
None
See application file for complete search history.

*Primary Examiner* — Laura B Goddard
(74) *Attorney, Agent, or Firm* — Oliff PLC (57) ABSTRACT

A hybridoma cell line NM002-1 secreting an anti-human pancreatic cancer monoclonal antibody and deposited under CCTCC Accession NO: C201173. Also, an anti-human pancreatic cancer monoclonal antibody NJ002-1 secreted by the hybridoma cell line NM002-1 and use thereof.

7 Claims, 3 Drawing Sheets

ANTI-PANCREATIC CANCER MONOCLONAL ANTIBODY AND USE THEREOF

BACKGROUND

Technical Field

The present invention relates to the field of medical diagnosis, and to an anti-pancreatic cancer monoclonal antibody and use thereof.

Related Art

Pancreatic cancer is a tumor having a high degree of malignancy, rapid development and poor prognosis, accounting for about 1-4% of all kinds of malignant tumors of the body, and accounting for 8-10% of the malignant tumors of digestive tract. Because of the inconspicuous onset and non-typical clinical symptoms, the early diagnosis of pancreatic cancer is difficult, and most patients are already in the middle-late stage upon treatment. The anatomical position of pancreas is deep, and adjacent to abdominal major organs and great vessels, and the pancreatic cancer is highly invasive, so the majority of patients lose the chance of receiving radical surgery. The tumor is insensitive to radiotherapy and chemotherapy, prone to distant metastasis and early local recurrence, and poor in the comprehensive treatment results, resulting in a 5-year survival rate of less than 5%.

Carbohydrate antigen 19-9 (CA19-9) is sialyl-lacto-N-fucopentaose II, which is a sialylated Lewis(a) blood group antigen obtained by immunization of mice in 1979 by Koprowski et al. The positive rate in the serum of pancreatic cancer patients is up to 70%-85%, and is still the most commonly used serum tumor marker in clinic at present. Ni et al reported that the sensitivity for diagnosis of pancreatic cancer with CA19-9 is up to 80%, and the specificity is only 43%. Especially in some benign diseases (such as biliary obstruction, pancreatitis and cirrhosis, etc.), elevated CA19-9 may also occur, so the less high specificity causes many inconveniences to the clinicians.

SUMMARY

In view of the disadvantages existing in the prior art, an object of the present invention is to provide an anti-pancreatic cancer monoclonal antibody. Another object of the present invention is to provide a hybridoma cell secreting the monoclonal antibody. A further object of the present invention is to provide the use of the monoclonal antibody and its specific antigen. The objects of the present invention can be achieved through the following technical solutions.

A hybridoma cell line NM002-1 secreting an anti-human pancreatic cancer monoclonal antibody is provided, which is deposited in China Center for Type Culture Collection (CCTCC) on Aug. 31, 2011 under CCTCC Accession NO: C201173.

An anti-human pancreatic cancer monoclonal antibody NJ002-1 secreted by the hybridoma cell line NM002-1 deposited under CCTCC Accession NO: C201173 is also provided.

Use of the monoclonal antibody NJ002-1 in the preparation of a diagnostic agent for pancreatic cancer is also provided.

Use of the monoclonal antibody NJ002-1 preferably in the preparation of an agent for early diagnosis of pancreatic cancer or for assisted diagnosis of pancreatic cancer is also provided. The diagnostic agent preferably includes an immunohistochemical detection reagent or a serum immunoassay reagent. The serum immunoassay reagent is further preferably an ELISA reagent.

Use of the monoclonal antibody NJ002-1 in the preparation of a diagnostic agent for prognosis of pancreatic cancer is also provided.

Use of a specific antigen of the monoclonal antibody NJ002-1 as a detection target in the preparation of a diagnostic or prognostic agent for pancreatic cancer is also provided.

Use of the monoclonal antibody NJ002-1 in the preparation of a drug for treating pancreatic cancer is also provided.

Use of a specific antigen of the monoclonal antibody NJ002-1 as a target in the preparation of a drug for treating pancreatic cancer is also provided.

Beneficial Effects:

In the present invention, the human pancreatic cancer cell line SW1990 is used as an immunogen, and a hybridoma cell line NM002-1 (CCTCC Accession NO: C201173) capable of stably secreting anti-human pancreatic cancer monoclonal antibody is screened by using a hybridoma technology. The monoclonal antibody NJ002-1 secreted by the hybridoma (CCTCC Accession NO: C201173) has high yield and high titer, and is specifically reactive to pancreatic cancer cell lines, and non-reactive or lowly reactive to normal pancreatic cells, healthy human PBMC and some other common tumor cell lines (lung cancer, liver cancer, breast cancer and colon cancer).

Immunohistochemical results show that the expression of NJ002-1 specific antigen is higher in pancreatic cancer tissues than in benign pancreatic tissues (76.7% vs. 17.6%, $p<0.001$). Further analysis shows that the positive expression rate of the antigen in patients with poorly differentiated pancreatic cancer is higher than that in patients with well-differentiated pancreatic cancer (82.4% vs. 62.2%, $p=0.022$). In the patients with high tumor infiltration and lymph node metastasis, the positive expression rate of the antigen is higher than that in the patients with low tumor infiltration and no lymph node metastasis (83.0% vs 60.0%, $p=0.010$; 91.2% vs 63.9%, $p<0.001$), respectively. The difference is statistically significant. Survival analysis shows that patients with positive antigen expression have a shorter survival time than those with negative expression ($p=0.021$).

Double antibody sandwich ELISA shows that the expression of the antigen in the serum of pancreatic cancer patients is higher than that in the healthy individuals ($p<0.05$). The sensitivity and specificity of ELISA for the detection of NJ002-1 specific antigen in serum are 50.6% and 90.0% in the diagnosis of pancreatic cancer patients respectively. The expression of NJ002-1 specific antigen is closely related to the differentiation, infiltration, lymph node metastasis and prognosis of pancreatic cancer. Meanwhile, the positive detection rate and specificity of the antigen in the serum of patients with pancreatic cancer are high.

In addition, although the detection rate of serum NJ002-1 specific antigen in 85 patients with pancreatic cancer is lower than that of CA19-9, the positive rate of combined detection of the two antigens is 86.8% (79/85), which is significantly higher than that of CA19-9 (75.8%, 69/85) alone. The difference is statistically significant ($x^2=5.221$, $P<0.05$). The combined detection of the two antigens can overcome the defect of poor specificity of CA19-9. It can be seen that NJ002-1 is expected as a diagnostic reagent for pancreatic cancer to further enhance the sensitivity and specificity of pancreatic cancer detection.

In summary, NJ002-1 specific antigen is expected to serve as a new tumor marker for the diagnosis of pancreatic cancer and prediction of the patient prognosis, and the monoclonal antibody NJ002-1 in the diagnosis of pancreatic cancer is effected.

In addition, the monoclonal antibody NJ002-1 can effectively inhibit the clone formation of pancreatic cancer cells SW1990 on soft agar, and the degree of inhibition is positively correlated with the antibody concentration. The monoclonal antibody NJ002-1 can significantly inhibit the growth of human pancreatic cancer xenografts in nude mice, and the degree of inhibition is positively correlated with the concentration of antibody. Therefore, the monoclonal antibody NJ002-1 is expected to be a drug for the treatment of pancreatic cancer.

BRIEF DESCRIPTION OF THE DRAWINGS

Note: The area under the curve is 0.831 (the standard error is 0.041, with a 9% confidence interval of 0.751-0.912).

FIG. 4 shows colonies formed with SW1990 on soft agar (×100), in which

A. Control group; B. 200 µg/ml Ab; C. 400 µg/ml Ab; D. 800 µg/ml Ab.

Deposition Information of Biomaterials

The hybridoma cell line NM002-1 is deposited in China Center for Type Culture Collection (CCTCC) (Wuhan University, 299 Bayi Road, Wuchang, Wuhan, Luojiashan 430072, China) on Aug. 31, 2011 under CCTCC Accession NO: C201173.

DETAILED DESCRIPTION

Example 1: Preparation of Hybridomas 1.1. Immunization of animals: 6-8-week-old female BALB/c mice were immunized 4 times by intraperitoneally injecting $2 \times 10^6$ SW1990 cells per injection at an interval of 3 weeks. Before each immunization, blood samples were collected from the inner canthus of mice and the serum antibody titers of the mice were detected by indirect ELISA. When the serum antibody titers in the immunized mice reached the maximum and did not increase any longer, the mouse spleen cells were fused. 3 days before fusion, boost immunization was performed once.

1.2. Indirect ELISA: The SW1990 cells were seeded on a 96-well plate at a density of $2 \times 10^5$/well. After growth to 80% confluence, the cells were fixed with 95% ethanol, washed 3 times with PBS, and permeabilized with 0.2% Triton-X-100 for 20 min. After blocking for 2 h with 50 g/L BSA at 37° C., 100 µL of various dilutions of serum from the immunized mice was added respectively and incubated at 37° C. for 1 h. After washing 3 times with PBS, 100 µL of 1:1000 dilution of HRP-labeled goat anti-mouse IgG was added and incubated at 37° C. for 45 min. After washing with PBS, TMB chromogen solution was added and incubated at 37° C. for 10 min before the reaction was terminated. The absorbance (A) at 450 nm was measured with a microplate reader. The serum (1:1000) from unimmunized mice was used as a negative control.

1.3. Cell fusion. The spleen of the immunized mice was ground into a cell suspension and fused with the myeloma cell SP2/0 in a logarithmic growth phase (Yao Xiaoling, Liu Xiaoyan, Wu Qiang, et al. Preparation of monoclonal antibody against human lung cancer and purification of its antigen by the immunoaffinity chromatography [J]. Chinese Journal of Immunology, 2006, 22 (12): 1140-1145.). 960 wells were fused at first. Cell clones appeared 1 week after fusion, and hybridoma cells were present in 800 wells, with the fusion rate being about 83%. Following the method in 1.2, indirect ELISA was conducted to screen positive hybridoma cells (where the serum from the immunized mice in indirect ELISA of 1.2 was replaced by the hybridoma cell culture supernatant), and the cells were transferred and sub-cloned by four limiting dilutions. Two hybridoma cell lines NM002-1 and NM002-2 were obtained which stably secret anti-SW1990 mAb and are the most positive.

Example 2: Preparation and Purification of Monoclonal Antibody Containing Ascitic Fluid Female BALB/c mice (8-10 weeks old) were injected intraperitoneally with 0.5 mL of paraffin oil. After 10 days, well grown hybridoma cells NM002-1 and NM002-2 were respectively injected intraperitoneally in an amount of about $1 \times 10^6$ cells/animal. After 1 to 2 weeks, the ascitic fluid was drawn and stood at 37° C. for 1 hr and then overnight at 4° C. On the following day, the ascitic fluid was centrifuged, purified by Protein G affinity chromatography to give purified monoclonal antibody NJ002-1 and NJ002-2.

Example 3: Identification of Monoclonal Antibodies 3.1. Identification Ig subclasses of the monoclonal antibodies: The purified monoclonal antibodies were 1:10000 diluted with PBS following the instructions for the assay kit. The subclasses of the monoclonal antibodies NJ002-1 and NJ002-2 are both IgG, with the light chain being the kappa chain.

3.2. Titer determination of monoclonal antibodies: The purified monoclonal antibodies NJ002-1 and NJ002-2 were respectively diluted with PBS, and each 100 µL was added to a 96-well plate coated with SW1990 cells. The $A_{450}$ value was determined by indirect ELISA. The titer of the monoclonal antibody was the maximum dilution at which the monoclonal antibody is immunoreactive to the coated cells. The titer of the monoclonal antibody NJ002-1 was $8 \times 10^6$, and the titer of the monoclonal antibody NJ002-2 was $4 \times 10^6$. The hybridoma cell line NM002-1 was deposited in the China Center for Type Culture Collection (CCTCC) (Wuhan university, Wuhan) on Aug. 31, 2011 under the CCTCC Accession NO: C201173.

3.3. Chromosome identification: The hybridoma cell line NM002-1 in logarithmic growth phase was treated for 8 hrs with colchicine. The cells were harvested and centrifuged onto glass slides. The cells were treated with a 0.075 mol/L KCl hypotonic solution, fixed with methanol/glacial acetic acid, and stained for 10 min with 10% Giemsa. The chromosomes were microscopically observed. The number of the chromosomes in the hybridoma cells ranged from 100 to 106, because the number of the chromosomes in the mouse cells was 40 and the average number of the chromosomes in the SP2/0 cells was 62 to 68. It was confirmed that the chromosomes in the hybridoma cells were from the spleen cells of the immunized mice and the mouse myeloma cells SP2/0, and were of the chromosome karyotype of hybridoma cells.

3.4. Specificity identification of monoclonal antibody: Indirect ELISA analysis was carried out with the purified monoclonal antibody NJ002-1, and the 8 cell lines above and healthy human PBMC respectively, to observe the presence or absence of a positive reaction. The results showed that monoclonal antibody NJ002-1 is strongly reactive only to the antigens of pancreatic cancer cells (SW1990, Panc-1 and BxPC-3), but not to the antigens of other tumor cells (SPCA1, HepG2, Colo205 and ZR-75-30), normal human pancreatic cells (HPDE6c7), and healthy PBMC.

Example 4

1. Source of Specimen

Experimental tissue specimens were from patients undergoing pancreatic resection (120 cases of pancreatic cancer and 17 cases of benign pancreatic disease) in the First Affiliated Hospital of Nanjing Medical University in 2009 to 2014. All patients had not received radiotherapy or chemotherapy before surgery, and were diagnosed by pathological examination. The corresponding paraffin-embedded tumor tissue specimens were checked. All the specimens were fixed with 10% formalin and embedded in paraffin, and were archived and provided by the pathology department of the First Affiliated Hospital of Nanjing Medical University. Of the 120 patients with pancreatic cancer, 64 were male and 56 were female, with a median age of 62 years. TNM staging was performed according to the standard of AJCC cancer staging manual (2014 Edition). There were 26 cases in stage I, 80 cases in stage II, 5 cases in stage III, 7 cases in stage IV, and 2 cases lacking staging data. There were 30 cases in T1 and T2, 88 cases in T3 and T4, and 2 cases lacking the infiltration depth data. There were 61 cases having no lymph node metastasis, and 57 cases having lymph node metastasis. Degree of differentiation was evaluated according to the WHO classification criteria of pancreatic cancer in 2004 showing that there were 37 cases of highly differentiated carcinoma, 68 cases of lowly differentiated carcinoma and 15 cases having no data of degree of differentiation.

17 cases of benign pancreatic diseases included 12 cases of pancreatic serous cystadenoma, 2 cases of pancreatic pseudocyst and 3 cases of pancreatitis. Details are shown in Table 1.

TABLE 1

Basic information of patients with pancreatic cancer

| Clinicopathological parameters | Pancreatic cancer (n = 89) n |
|---|---|
| Age (years) | |
| ≤62 | 62 |
| >62 | 58 |
| Gender | |
| Male | 64 |
| Female | 56 |
| Maximum tumor size (cm) | |
| ≤3 | 49 |
| >3 | 64 |
| No data | 7 |
| Degree of differentiation | |
| High (I/I-II/II) | 37 |
| Low (II-III/III) | 68 |
| No data | 15 |
| Degree of infiltration | |
| T1/T2 | 30 |
| T3/T4 | 88 |
| No data | 2 |
| Lymph node metastasis | |
| N0 | 61 |
| N1 | 57 |
| No data | 2 |
| TNM staging | |
| I/II | 106 |
| III/IV | 12 |
| No data | 2 |

2. Immunohistochemical Staining

The specific process of immunohistochemical staining might be made reference to Han Yue, Wang Fang, Xu Ting, et al. Expression and clinical significance of NJ001-1 specific antigen in lung adenocarcinoma [J] Journal of Laboratory Medicine. 2013, 36 (10): 895-898. The primary antibody was the monoclonal antibody NJ002-1, 1% PBS was used as a negative control in place of the primary antibody, and the tumor tissue slice of diagnosed pancreatic cancer was used as a positive control. The fast enzyme-labeled goat anti-mouse/rabbit IgG polymer was purchased from Fuzhou Maixin Biotech. Co., Ltd and the DAB chromogen kit was purchased from Beijing Zhongshan Golden Bridge Biotechnology Co., Ltd.

Judgment of results: Based on the percentage of brown-yellow positive reaction and the degree of staining in the tumor cells, comprehensive judgment and analysis are made. The positive percentage is the percentage of positive cells per 200 tumor cells at high magnification, which is an average of 5 random measurements. The positive rate is scored as follows: 0 (positive percentage 0%), 1 (positive percentage 1-33%), 2 (positive percentage 34-66%), and 3 (positive percentage 67-100%). The degree of staining is scored as follows. No staining, light yellow, brown-yellow, and tan were scored as 0, 1, 2, and 3 respectively. The products of the scores of the two methods are 0, 1, 2, 3, 4, 6, and 9. The scores are divided into four levels including −(0), +(1, 2), ++(3, 4), and +++(6, 9), of which ++, and +++ were judged as positive expression.

3. Follow-Up

The collected 120 cases of patients with pancreatic cancer were treated by telephone or outpatient follow up, and the complete follow-up information of a total of 72 patients was obtained, with a follow-up rate of 60%. The survival time was calculated on a monthly basis with the date of surgery as the starting point for observation, which was a period of time from the date of surgery to the date of death due to the recurrence or metastasis of pancreatic cancer, or the deadline for follow-up. The cases of non-tumor deaths and complete loss of follow-up were statistically subjected to censored data processing.

4. Statistical Method

SPSS16.0 statistical software was used for data analysis. The count data was analyzed using the $\chi^2$ test or Fisher exact test. The survival analysis was conducted using Kaplan-Meier curve, and the lifetimes of the two groups were compared using log-rank test. Multi-factor Cox proportional hazards model for analysis by stepwise introduction-culling method was performed. The difference was statistically significant when $p<0.05$.

5. Results

5.1. Expression of NJ002-1 Specific Antigen in Tissues of Pancreatic Cancer and Benign Pancreatic Diseases In the experiment, the tissue samples included tissues of 120 cases of pancreatic cancer and 17 cases of pancreatic benign disease, and all the immunohistochemical test results were shown in Table 2-3.

TABLE 2

List of immunohistochemical results of NJ002-1 specific antigen in paraffin-embedded tissue sections from patients with pancreatic cancer

| No. | Pathological grading | T | N | M | TNM staging | NJ002-1 specific antigen |
|---|---|---|---|---|---|---|
| 1 | II-III | 3 | 1 | 0 | IIB | +++ |
| 2 | II-III | 3 | 1 | 0 | IIB | +++ |
| 3 | I-II | 2 | 1 | 0 | IIB | ++ |
| 4 | I-II | 3 | 0 | 0 | IIA | + |
| 5 | II-III | 3 | 1 | 0 | IIB | +++ |
| 6 | II-III | 3 | 0 | 0 | IIA | + |
| 7 | I-II | 3 | 1 | 0 | IIB | ++ |
| 8 | — | 2 | 0 | 0 | IB | +++ |
| 9 | II-III | 1 | 0 | 0 | IA | +++ |
| 10 | — | 4 | 1 | 0 | III | ++ |
| 11 | II-III | 3 | 1 | 0 | IIB | ++ |
| 12 | II-III | 3 | 1 | 0 | IIB | ++ |
| 13 | II | 3 | 0 | 0 | IIA | +++ |
| 14 | II-III | 3 | 0 | 0 | IIA | ++ |
| 15 | II | 3 | 1 | 1 | IV | +++ |
| 16 | II-III | 4 | 0 | 0 | III | +++ |
| 17 | II | 3 | 0 | 0 | IIA | ++ |
| 18 | — | 2 | 0 | 0 | IB | ++ |
| 19 | II-III | 3 | 1 | 0 | IIB | ++ |
| 20 | II | 3 | 1 | 0 | IIB | +++ |
| 21 | II | 3 | 0 | 0 | IIA | + |
| 22 | II-III | 3 | 0 | 0 | IIA | ++ |
| 23 | II | 2 | 1 | 0 | IIB | ++ |
| 24 | III | 3 | 0 | 0 | IIA | + |
| 25 | I-II | 3 | 1 | 0 | IIB | ++ |
| 26 | — | 4 | 1 | 0 | III | +++ |
| 27 | II-III | 3 | 0 | 0 | IIA | ++ |
| 28 | II | 3 | 0 | 0 | IIA | +++ |
| 29 | — | 2 | 0 | 1 | IV | +++ |
| 30 | — | 0 | 0 | 0 | Tis | ++ |
| 31 | — | 3 | 0 | 0 | IIA | + |
| 32 | II-III | 3 | 0 | 0 | IIA | +++ |
| 33 | I-II | 2 | 0 | 0 | IB | + |
| 34 | II | 3 | 0 | 0 | IIA | + |
| 35 | II-III | 3 | 0 | 0 | IIA | +++ |
| 36 | II-III | 3 | 1 | 0 | IIB | ++ |
| 37 | II-III | 4 | 1 | 1 | IV | +++ |
| 38 | II-III | 3 | 1 | 0 | IIB | +++ |
| 39 | II-III | 3 | 0 | 0 | IIA | ++ |
| 40 | II | 3 | 0 | 0 | IIA | + |
| 41 | — | 4 | 0 | 0 | III | +++ |
| 42 | II-III | 3 | 1 | 0 | IIB | ++ |
| 43 | II-III | 3 | 1 | 0 | IIB | +++ |
| 44 | — | 3 | 0 | 0 | IIA | +++ |
| 45 | II-III | 2 | 1 | 0 | IIB | + |
| 46 | II | 3 | 0 | 0 | IIA | + |
| 47 | II | 3 | 1 | 0 | IIB | +++ |
| 48 | II | 3 | 1 | 0 | IIB | + |
| 49 | II-III | 2 | 0 | 0 | IB | − |
| 50 | II-III | 3 | 1 | 0 | IIB | ++ |
| 51 | II-III | 3 | 1 | 0 | IIB | + |
| 52 | II-III | 3 | 1 | 0 | IIB | +++ |
| 53 | II-III | 3 | 1 | 0 | IIB | +++ |
| 54 | II | 3 | 1 | 0 | IIB | + |
| 55 | III | 3 | 1 | 0 | IIB | +++ |
| 56 | II-III | 3 | 0 | 0 | IIA | +++ |
| 57 | II-III | 3 | 1 | 0 | IIB | +++ |
| 58 | III | — | — | — | — | ++ |
| 59 | II-III | 2 | 0 | 0 | IB | − |
| 60 | II-III | 3 | 1 | 0 | IIB | ++ |
| 61 | II-III | 3 | 1 | 0 | IIB | ++ |
| 62 | III | 3 | 1 | 0 | IIB | +++ |
| 63 | II-III | 3 | 1 | 0 | IIB | +++ |
| 64 | I | 0 | 0 | 0 | Tis | − |
| 65 | II-III | 3 | 1 | 0 | IIB | +++ |
| 66 | II-III | 3 | 0 | 0 | IIA | ++ |
| 67 | II-III | 1 | 0 | 0 | IA | − |
| 68 | — | 4 | 1 | 1 | IV | ++ |
| 69 | II | 3 | 1 | 0 | IIB | ++ |
| 70 | II-III | 3 | 0 | 0 | IIA | − |
| 71 | II-III | 3 | 1 | 0 | IIB | +++ |
| 72 | II-III | 3 | 1 | 0 | IIB | +++ |
| 73 | II-III | 3 | 1 | 0 | IIB | ++ |
| 74 | II | 3 | 0 | 0 | IIA | +++ |
| 75 | I-II | 3 | 0 | 0 | IIA | ++ |
| 76 | II-III | 3 | 0 | 0 | IIA | ++ |
| 77 | II-III | 3 | 1 | 0 | IIB | +++ |
| 78 | II-III | 3 | 1 | 0 | IIB | +++ |
| 79 | II-III | 3 | 0 | 0 | IIA | ++ |
| 80 | I | 3 | 1 | 0 | IIB | +++ |
| 81 | II-III | 3 | 0 | 0 | IIA | +++ |
| 82 | II | 3 | 0 | 0 | IIA | +++ |
| 83 | — | 3 | 1 | 0 | IIB | ++ |
| 84 | II-III | 3 | 1 | 0 | IIB | ++ |
| 85 | II-III | 2 | 0 | 0 | IB | ++ |
| 86 | II-III | 3 | 0 | 0 | IIA | + |
| 87 | I-II | 2 | 0 | 0 | IB | + |
| 88 | II-III | 3 | 1 | 0 | IIB | +++ |
| 89 | II-III | 3 | 0 | 0 | IIA | +++ |
| 90 | II | 2 | 0 | 0 | IB | + |
| 91 | I | 3 | 0 | 0 | IIA | + |
| 92 | I-II | 3 | 1 | 0 | IIB | + |
| 93 | I | 1 | 0 | 0 | IA | − |
| 94 | I-II | 1 | 0 | 0 | IA | ++ |
| 95 | I | 3 | 1 | 0 | IIB | +++ |
| 96 | II | 3 | 0 | 0 | IIA | +++ |
| 97 | I-II | 2 | 0 | 0 | IB | ++ |
| 98 | I | 1 | 0 | 0 | IA | ++ |
| 99 | I-II | 3 | 1 | 0 | IIB | +++ |
| 100 | I | 2 | 0 | 0 | IB | ++ |
| 101 | II | 3 | 0 | 0 | IIA | +++ |
| 102 | III | 3 | 1 | 0 | IIB | +++ |
| 103 | II-III | 1 | 0 | 0 | IA | ++ |
| 104 | II-III | 4 | 1 | 0 | III | +++ |
| 105 | II-III | 3 | 1 | 0 | IIB | +++ |
| 106 | III | 1 | 0 | 0 | IA | ++ |
| 107 | II-III | 3 | 1 | 0 | IIB | +++ |
| 108 | III | 4 | 1 | 1 | IV | +++ |
| 109 | III | 2 | 0 | 0 | IB | − |
| 110 | II-III | 4 | 1 | 1 | IV | +++ |
| 111 | II-III | 2 | 0 | 0 | IB | − |
| 112 | II-III | 3 | 1 | 0 | IIB | +++ |
| 113 | III | 4 | 1 | 1 | IV | +++ |
| 114 | II-III | 1 | 0 | 0 | IA | ++ |
| 115 | II-III | 1 | 0 | 0 | IA | ++ |
| 116 | III | — | — | — | — | − |
| 117 | — | 3 | 1 | 0 | IIB | ++ |
| 118 | — | 2 | 0 | 0 | IB | − |
| 119 | — | 1 | 0 | 0 | IA | ++ |
| 120 | — | 1 | 0 | 0 | IA | ++ |

TABLE 3

List of immunohistochemical results of NJ002-1 specific antigen in paraffin-embedded tissue sections from patients with benign pancreatic diseases

| No. | Disease | NJ002-1 specific antigen |
|---|---|---|
| 1 | Serous cystadenoma | – |
| 2 | Serous cystadenoma | + |
| 3 | Pancreatic cyst | – |
| 4 | Serous cystadenoma | + |
| 5 | Serous cystadenoma | – |
| 6 | Serous cystadenoma | – |
| 7 | Serous cystadenoma | – |
| 8 | Serous cystadenoma | – |
| 9 | Serous cystadenoma | ++ |
| 10 | Serous cystadenoma | + |
| 11 | Pancreatic cyst | + |
| 12 | Serous cystadenoma | – |
| 13 | Pancreatitis | ++ |
| 14 | Serous cystadenoma | + |
| 15 | Serous cystadenoma | ++ |
| 16 | Pancreatitis | – |
| 17 | Pancreatitis | – |

Figure 1:
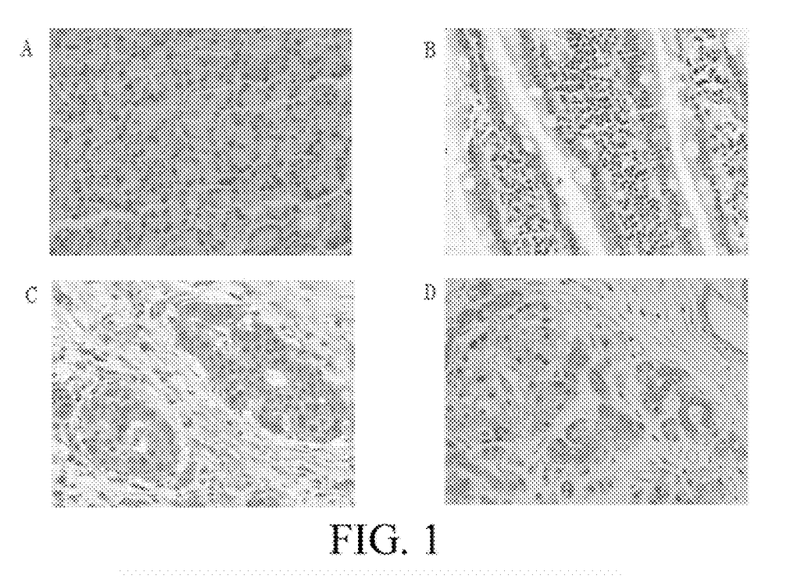
FIG. 1 shows immunohistochemical results of NJ002-1 specific antigen in pancreatic cancer and benign pancreatic diseases (×200), in which Panel A shows benign pancreatic disease, and Panels B-D show pancreatic cancer+, ++, and +++.

The expression of NJ002-1 specific antigen was mainly in cytoplasm, which was consistent with the result of previous studies. In the vast majority of tissues of benign pancreatic disease, no antigen was expressed, and the antigen was weakly expressed in a small number of tissues. Most of the tissues of pancreatic cancer showed many brown-yellow or tan particles, indicating that the expression of the antigen was significantly enhanced (FIG. 1).

The positive rates of NJ002-1 specific antigen in 120 cases of pancreatic cancer and 17 cases of benign pancreatic diseases were 76.7% and 17.6%, respectively, and there was a statistically significant difference therebetween (P<0.001, Table 4).

TABLE 4

Expression of NJ002-1-specific antigen in pancreatic cancer and benign pancreatic diseases

| Group | Number of cases | NJ002-1 specific antigen Negative | NJ002-1 specific antigen Positive | Positive rate (%) | P value |
|---|---|---|---|---|---|
| Pancreatic cancer | 120 | 28 | 92 | 76.7 (92/120) | <0.001 |
| Benign pancreatic diseases | 17 | 14 | 3 | 17.6 (3/17) | |

5.2. Relationship Between the Expression of NJ002-1 Specific Antigen and the Clinicopathological Features of Pancreatic Cancer The positive rates of NJ002-1 specific antigen expression were 82.4% vs. 62.2% in lowly differentiated and highly differentiated tumor groups, respectively; 60.0% vs. 83.0% in groups with an infiltration depth of T1/T2 and T3/T4 respectively; and 63.9% vs. 91.2% in groups having no or having lymph node metastasis, and there was statistical difference therebetween as indicated by $\chi^2$ test. There was no direct relation between the antigen expression and the age, gender, and tumor size of the pancreatic cancer patients. The positive rate of the antigen expression was 100% in 12 patients with stage III/IV pancreatic cancer, and there was no statistically significant difference as compared to that in the patients with stage I/II pancreatic cancer (Table 5).

TABLE 5

The Relationship between the expression of NJ002-1 specific antigen and the clinicopathological features of patients with pancreatic cancer

| Clinicopathological features | Number of cases | Number of positive cases | Positive rate (%) | p |
|---|---|---|---|---|
| Age (years) | | | | |
| ≤62 | 62 | 47 | 75.8 | 0.818 |
| >62 | 58 | 45 | 77.6 | |
| Gender | | | | |
| Female | 56 | 40 | 71.4 | 0.204 |
| Male | 64 | 52 | 81.3 | |
| Tumor size (cm) | | | | |
| ≤3 | 49 | 37 | 75.5 | 0.596 |
| >3 | 64 | 51 | 79.7 | |
| No data | 7 | | | |
| Degree of differentiation | | | | |
| High (I/I-II/II) | 37 | 23 | 62.2 | 0.022 |
| Low (II-III/III) | 68 | 56 | 82.4 | |
| No data | 15 | | | |
| Infiltration depth | | | | |
| T1/T2 | 30 | 18 | 60.0 | 0.010 |
| T3/T4 | 88 | 73 | 83.0 | |
| No data | 2 | | | |
| Lymph node metastasis | | | | |
| N0 | 61 | 39 | 63.9 | <0.001 |
| N1 | 57 | 52 | 91.2 | |
| No data | 2 | | | |
| Clinical staging | | | | |
| I/II | 106 | 79 | 74.5 | 0.066* |
| III/IV | 12 | 12 | 100.0 | |
| No data | 2 | | | |

*Analyzed by Fisher exact test, and the rest are analyzed by $\chi^2$ test

Figure 2:
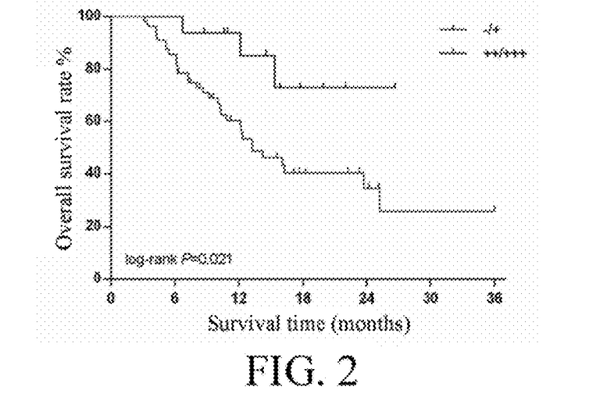
FIG. 2 shows survival curves of patients with pancreatic cancer.
Figure 3:
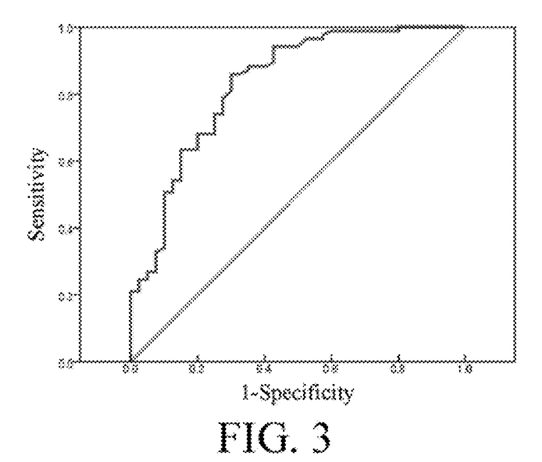
FIG. 3 shows an ROC curve of NJ002-1 specific antigen in the serum of patients with pancreatic adenocarcinoma.

5.3. Relationship Between the Expression of NJ002-1 Specific Antigen and the Prognosis of Patients with Pancreatic Cancer The patients were followed up to May 31, 2015, with an endpoint of death. A total of 72 patients with complete data were included in our study. The median follow-up time was 12.1 (3.1-36) months. 16 patients were included in the group with negative expression of NJ002-1 specific antigen, of which 3 were died. 56 patients were included in the positive group, of which 31 were died. The median survival time in the positive group (n=56) was 13.2 months and was 14.6 months in the negative group (n=16). There was a significant difference in the survival time between the groups with positive or negative expression of NJ002-1 specific antigen, and the higher the antigen expression level was, the shorter the survival time would be (p=0.021, FIG. 2).

The above experimental results showed that: NJ002-1 specific antigen is highly expressed in most of the pancreatic cancer tissues, but poorly expressed in tissues with benign pancreatic disease, suggesting that the antigen may affect the progress of pancreatic cancer. Further analysis confirmed that the expression of NJ002-1 specific antigen is closely related to the degree of differentiation, the infiltration depth, and the lymph node metastasis of pancreatic cancer. It can be seen that the high expression of the antigen may suggest the strong tumor invasion and metastasis. Therefore, the monoclonal antibody NJ002-1 can be used in the preparation of an immunohistochemical reagent for the diagnosis, prognosis and prediction of tumor invasion and metastasis of pancreatic cancer.

Example 5

1. Blood sample: 107 serum samples were collected from patients with pancreatic cancer who were admitted to the First Affiliated Hospital of Nanjing Medical University in June 2014 to May 2015, including 85 patients with pancreatic cancer, and 22 patients with benign pancreatic tumors, where the 22 patients with benign pancreatic tumors included 4 patients pancreatic (pseudo) cyst and 18 patients with serous cystic tumors. All the patients received radical surgery and were diagnosed by histopathological examination, and none of the patients underwent radiotherapy or chemotherapy prior to surgery. At the same time, serum samples were collected from 40 healthy subjects. The clinicopathological parameters are shown in Table 6.

TABLE 6

Clinicopathological parameters of the patients with different types of pancreatic tumors and the subjects in the control group

| Group | Number of cases | Age (number of cases) ≤60 years | Age (number of cases) >60 years | Median age years | Gender (number of cases) Male | Gender (number of cases) Female |
|---|---|---|---|---|---|---|
| Pancreatic tumor | 85 | 33 | 52 | 62 | 44 | 41 |
| Benign pancreatic tumor | 22 | 16 | 6 | 56 | 8 | 14 |
| Healthy Control group | 40 | 35 | 5 | 35 | 22 | 18 |

2. Methods 2.1. Specimen collection and treatment: 2 ml venous blood was collected from the patients by using a vacuum blood collection tube containing a serum separating medium respectively before and 10 days after operation, stood for 20 min at room temperature, and centrifuged for 10 min at 2100×g. The upper serum was transferred, and then centrifuged for 10 min at 4° C., and 16000×g. The upper cell-free serum was aspirated and packaged into aliquots of 130 μl per tube, and stored at −70° C.

2.2. Cell culture: SPC-A1 cells were grown in RPMI 1640 medium containing 10% fetal bovine serum, 100 U/mL penicillin and 100 ng/mL streptomycin, and cultured in an incubator at 37° C., 5% $CO_2$.

2.3. Double-antibody sandwich ELISA: A 96-well ELISA plate was coated with anti-SPC-A1 rabbit polyclonal antibody (1.782 μg/ml) in an amount of 100 μl per well, stood overnight at 4° C., and washed three times. 3% BSA was added in an amount of 300 μl per well. The plate was blocked overnight at 4° C., and washed 3 times. 50 μl of serum to be assayed was added per well, incubated for 2 hrs at 37° C., and washed six times. The primary antibody NJ002-1 (5 mg/ml, 1:1000 dilution) was added in an amount of 100 μl per well (excluding the blank wells), incubated for 1 hr at 37° C., and washed six times. Goat anti-mouse IgG/HRP maker (1:2000) was added in an amount of 100 μl per well (excluding the blank wells), incubated for 30 min at 37° C., and washed six times. A freshly prepared chromogenic substrate solution was added in an amount of 100 μl per well, and developed for 10 min in the dark at room temperature. 50 μl of a stop solution was added to terminate the reaction. The absorbance (A) was read at 450 nm on a microplate reader. The positive and negative controls were SPC-A1 cell lysate and fetal bovine serum respectively, and the blank control did not contain any ingredients. The x±2 s, that is, 2.1 of the P/N value of the serum samples from 300 healthy subjects previously tested in our laboratory was used as the cut-off value.

2.4. Electrochemiluminescence detection of CA19-9: Synchronized detection of serum CA19-9 was conducted by using Roche Cobase602 Electrochemiluminescence Immunoassay analyzer, where the reagents, calibration fluid, and control materials were all provided by the manufacturer. The cut-off value of CA19-9 was 39 U/mL.

3. Statistical Treatment

SPSS19.0 software was used to analyze the data of this study. The positive rates of each group and before and after operation were compared using $\chi^2$ test or Fisher exact test, $P<0.05$ indicates statistically significant difference.

4. Results 4.1. Expression of NJ002-1 specific antigen in the serum of pancreatic cancer patients The positive rate of NJ002-1 specific antigen in pancreatic cancer was 50.6% (43/85), which was significantly higher than that in benign pancreatic tumor group and healthy control group (50.6% vs 18.2%, $\chi^2=7.451$, $P<0.05$; 50.6% vs, 10.0%, $\chi^2=10.098$, $P<0.05$). At the same time, the ROC curve analysis of the test results of 85 patients with pancreatic cancer and 40 healthy subjects showed that the corresponding area under curve AUC was 0.831 (standard error 0.041; 95% confidence interval 0.751-0.912). At a cut-off value of 2.1, the corresponding sensitivity was 50.6% and the specificity was 90.0%.

4.2. Use of NJ002-1 Specific Antigen Before and After Operation 85 patients with pancreatic cancer all received radical surgery of the pancreas, including 28 cases of pancreaticoduodenectomy, 28 cases of distal pancreatectomy, 24 cases of pylorus-preserving pancreaticoduodenectomy and 5 cases of pancreaticoduodenectomy in combination with vessel resection. The positive rates of NJ002-1 specific antigen expression in serum before and after radical surgery were 50.6% (43/85) and 23.5% (20/85), respectively, and the difference was statistically significant ($\chi^2=8.938$, $P<0.05$).

4.3. Comparison of Commonly Used Tumor Markers in Pancreatic Cancer with the Present Method Although the detection rate of serum NJ002-1 specific antigen in 85 patients with pancreatic cancer was lower than that of CA19-9, the positive rate of combined detection of the two antigens was 86.8% (79/85), which was significantly higher than that of CA19-9 (75.8% (69/85)) alone, and the difference was statistically significant ($\chi^2=5.221$, $P<0.05$), as shown in Table 7.

TABLE 7

Positive rate of NJ002-1 specific antigen and CA19-9 detected alone and in combination in 85 patients with pancreatic adenocarcinoma [n(%)]

| Item detected | Pancreatic cancer group (n = 85) |
|---|---|
| CA19-9 | 69 (75.8) |
| NJ002-1 specific antigen | 43 (50.6) |
| CA199 + NJ002-1 specific antigen | 79 (86.8) |

The above experimental results showed that: NJ002-1 specific antigen is not only highly expressed in pancreatic cancer tissues, but also has a higher expression in the serum of pancreatic cancer patients than in the serum of the healthy controls, suggesting that the tumor cells rich in the antigen may migrate into the blood vessels and thus enter into the blood circulation, thus providing a powerful basis for the antigen to serve as a molecular target in the diagnosis of pancreatic cancer. ROC curve analysis showed that the antigen is of practical value and has desirable sensitivity and specificity in the diagnosis of pancreatic cancer. Detection of NJ002-1 specific antigen in serum by double-antibody sandwich ELISA can provide a powerful evidence for the clinical diagnosis of pancreatic cancer. NJ002-1 specific antigen can be used as a new serum tumor marker of pancreatic cancer and is expected to be used in the early diagnosis of this disease.

Example 6: Clone Formation Test on Soft Agar

1. Method

3% agarose solution in saline was prepared, and then sterilized in an autoclave. Double-layered agarose gel was prepared in a 6-well cell culture plates, with the lower layer as a support layer. A L15 complete medium containing 10% FBS was mixed with 3% agarose at a ratio of 5:1, to prepare a medium containing 0.5% agarose, which was then added to the 6-well plate in an amount of 2 ml/well, and solidified by cooling at room temperature. Pancreatic cancer SW1990 cells in logarithmic growth phase were collected, prepared into a single cell suspension in complete medium, and incubated at 37° C. A suitable amount of the single cell suspension was fully mixed with 3% agarose solution and different concentrations of the monoclonal antibody NJ002-1 solution, and plated in an amount of 2 ml/well to prepare upper agar containing 0.3% agarose, where each well contained $2 \times 10^4$ cells, the final concentrations of the antibody were 0, 200 μg/ml, 400 μg/ml, 800 μg/ml, 1600 μg/ml, and 2000 μg/ml respectively, and each dose was triplicated. After the agar was solidified at room temperature, the plate was transferred to and cultured for 2 weeks in an incubator at 37° C. and 5% $CO_2$. The cells were counted under an inverted microscope, and a colony with 50 or more cells were determined as a clone. The clone formation rate and inhibition rate were calculated. Clone formation rate= (number of clones/number of inoculated cells)×100%; Inhibition rate=(1−clone formation rate in the experimental group/clone formation rate in the control group)×100%.

2. Results

Figure 4:
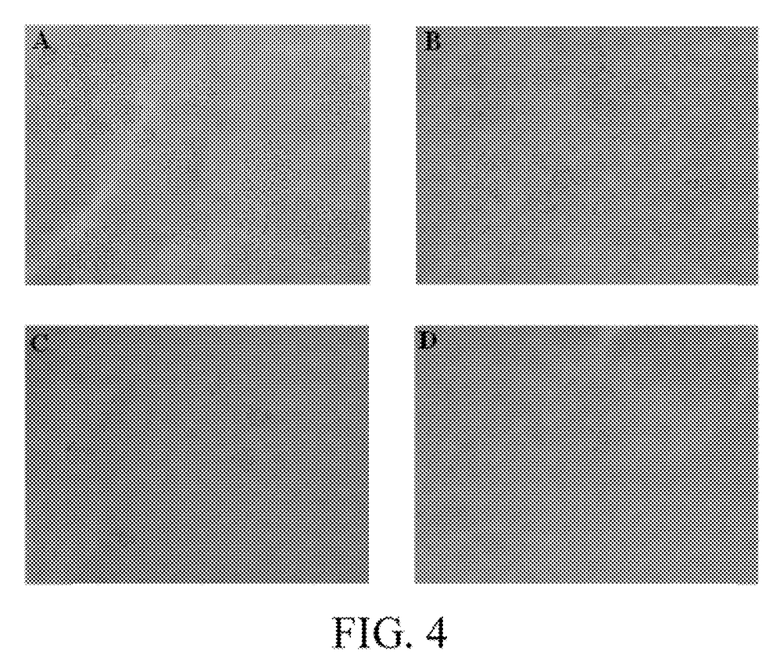

In the double-layered agar medium, the SW1990 cells in the control group grew vigorously, and cell colonies were generally formed in 7-10 days. After 2 weeks, the number of colonies was observed to significantly increase. The number of cells forming colonies was significantly reduced in the presence of the monoclonal antibody NJ002-1, and the colony was much smaller than the control group. Some of the cells could not grow in soft agar to form colonies, and existed as single scattered cells (FIG. 4).

The results of colony formation test in soft agar showed that the monoclonal antibody NJ002-1 can effectively inhibit the clone formation of the pancreatic cancer cells SW1990 in soft agar, and the degree of inhibition was positively correlated with the concentration of the antibody. In the presence of 200 μg/ml monoclonal antibody, the inhibition rate reached 29.79% after 2 weeks, and the inhibition rate in the group with 40 μg/ml monoclonal antibod was 65.96%. There was almost no clone growth in the groups with 800 μg/ml monoclonal antibody or higher (Table 8). Statistical analysis showed that the number of clones in the groups with 200 μg/ml and 400 μg/ml monoclonal antibody was significantly decreased compared with the control group (P<0.001, P<0.001). There was also significant difference between the number of clones in the groups with 200 μg/ml and 400 μg/ml monoclonal antibody (P<0.001).

TABLE 8

Effect of monoclonal antibody NJ002-1 on clone formation of SW1990 in soft agar (n = 3)

| Antibody concentration (μg/ml) | Number of clones (≥50 cells/clone) | Clone formation rate[a] (%) | Clone inhibition rate[b] (%) |
|---|---|---|---|
| 0 | 187 ± 5.43 | 0.94 | 0 |
| 200 | 132 ± 2.73* | 0.66 | 29.79 |
| 400 | 63 ± 4.82* | 0.32 | 65.96 |
| 800 | 0 | 0 | 100 |
| 1600 | 0 | 0 | 100 |
| 2000 | 0 | 0 | 100 |

Note:
*P < 0.001, compared with the control group;
^P < 0.001 compared with the group with 200 μg/ml monoclonal antibody Example 7: Experiment of Xenograft Model in Nude Mice 1. Method 25 nude mice were randomized into 5 groups, including a normal saline group, 3 monoclonal antibody groups (200 μg, 400 μg, and 800 μg) and a monoclonal antibody control group, each group having 5 animals. The nude mice in the normal saline group and the monoclonal antibody groups were subcutaneously inoculated with a SW1990 cell suspension in an amount of 2×106 cells/mouse via the right axilla. On the day of inoculation of the monoclonal antibody, the mice were injected intraperitoneally with 200 μl of different concentrations of the monoclonal antibody solution (containing 200 μg, 400 μg and 800 μg monoclonal antibody respectively). The mice were injected once daily for the first 5 days and then injected once every 3 days for 2 consecutive weeks (where cumulative 9 injections were performed). In the normal saline group, an equal volume of saline was used in place of the monoclonal antibody solution, and the injection time and route were the same. In the monoclonal antibody control group, 5 nude mice were injected intraperitoneally with merely 200 μl of the monoclonal antibody solution at a dosage of 800 μg of monoclonal antibody/animal. The injection time of the antibody was the same as that of the monoclonal antibody group. The activity, mental status, food intake and occurrence time of tumors were observed and record every day. Since the appearance of subcutaneous nodules, the long diameter (a) and short diameter (b) of the xenograft were measured by using a vernier caliper, and the xenograft volume was calculated by the formula V=ab2/2. Three weeks after the inoculation of tumor cells, the nude mice was sacrificed by cervical dislocation, the tumors were dissected and weighed. The tumor inhibition rate was calculated according to the formula: Tumor inhibition rate=(1−average tumor weight in the monoclonal antibody group/average tumor weight in the normal saline group)×100%.

2. Results

Figure 5:
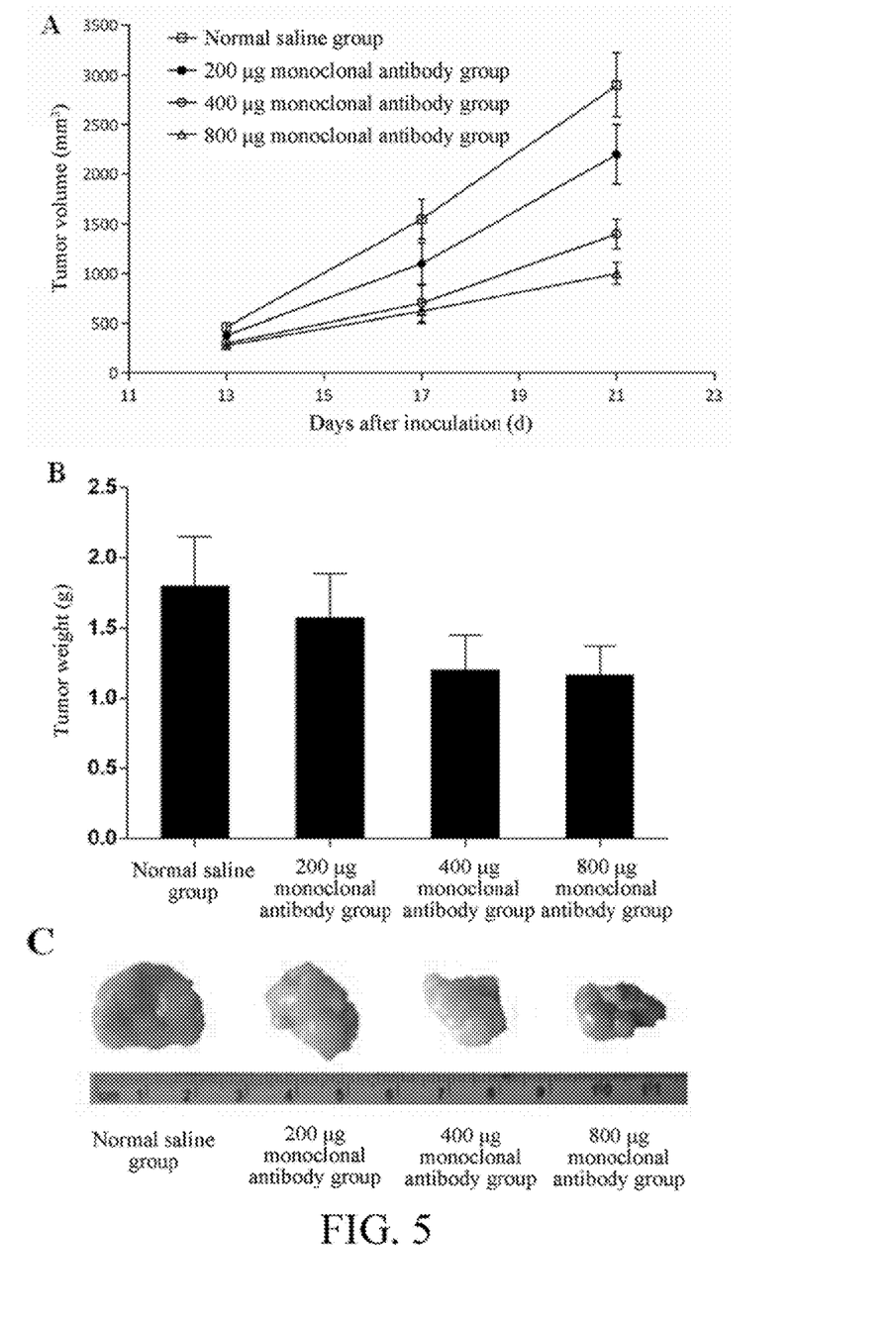
FIG. 5 shows inhibition of the monoclonal antibody NJ002-1 on the growth of SW1990 xenografts, in which Panel A shows tumor growth curves, Panel B shows average tumor weight, and Panel C shows tumors resected in each group.

On the 9th day after inoculation of cells, nodules were initially visually observed in the transplanted region in normal saline group. After 2 days, nodules were observed in the monoclonal antibody groups and the rate of tumor formation reached 100%. The tumor volume was measured from day 13 and observed until day 21. The mean tumor volume of mice in each group increased with the elapse of time. From the 17th day, the growth rate of tumor volume in the 400 μg and 800 μg monoclonal antibody groups was significantly slowed down compared with the normal saline group. By the end of observation, the difference persisted (P<0.001, P<0.001, FIG. 5A). The mice were sacrificed 3 weeks after inoculation of the cells, the tumors were separated and weighed. The average tumor weights in the normal saline group, and 200 μg, 400 μg, and 800 μg monoclonal antibody groups were (1.80±0.35) g, (1.57±0.32) g, (1.23±0.25) g, and (1.16±0.21) g respectively. As shown by comparison between groups by one-way analysis of variance, there was statistically significant difference between the tumor weight of the four groups of mice (F=5.410, P=0.009). Pairwise comparison showed that the average tumor weights of the 400 μg and 800 μg monoclonal antibody groups were significantly lower than that of the saline group (P=0.018, P=0.008). There was also a significant difference between the 200 μg and 800 μg monoclonal antibody groups (P=0.044). The tumor inhibition rates in the 200 μg, 400 μg, and 800 μg monoclonal antibody groups were 12.78%, 31.67% and 35.56% respectively from low to high (FIGS. 5B and C). By the end of the experiment, the mice in 800 μg monoclonal antibody control group were all observed alive, and in normal living state, and had good appetite and free movement, and no abnormal changes. The results showed that: the monoclonal antibody NJ002-1 can significantly inhibit the growth of human pancreatic cancer xenograft in vivo.

What is claimed is:

1. A hybridoma cell line NM002-1 secreting an anti-human pancreatic cancer monoclonal antibody, which is deposited in China Center for Type Culture Collection (CCTCC) on Aug. 31, 2011 under CCTCC Accession NO: C201173.

2. An anti-human pancreatic cancer monoclonal antibody NJ002-1 secreted by the hybridoma cell line NM002-1 deposited under CCTCC Accession NO: C201173 according to claim 1.

3. A diagnostic or prognostic agent comprising the monoclonal antibody NJ002-1 according to claim 2.

4. The diagnostic or prognostic agent according to claim 3, wherein the monoclonal antibody NJ002-1 is coupled to an immunohistochemical detection reagent or a serum immunoassay reagent.

5. The diagnostic or prognostic agent according to claim 4, wherein the serum immunoassay reagent is an ELISA reagent.

6. A method comprising: performing an immunoassay on a biological sample from an individual having or suspected of having pancreatic cancer, the method comprising: contacting the biological sample with the diagnostic or prognostic agent according to claim 3; and detecting binding of the agent to the biological sample.

7. A method of treating pancreatic cancer comprising: administering the monoclonal antibody NJ002-1 according to claim 2 to an individual having pancreatic cancer.

* * * * *